(12) United States Patent
Katsunuma

(10) Patent No.: US 11,617,830 B2
(45) Date of Patent: Apr. 4, 2023

(54) MEDICAL PUMP, METHOD OF CONTROLLING MEDICAL PUMP, AND MEDICAL PUMP SYSTEM

(71) Applicant: TERUMO KABUSHIKI KAISHA, Tokyo (JP)

(72) Inventor: Takayuki Katsunuma, Yokohama (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 497 days.

(21) Appl. No.: 16/811,376

(22) Filed: Mar. 6, 2020

(65) Prior Publication Data

US 2020/0206419 A1 Jul. 2, 2020

Related U.S. Application Data

(63) Continuation of application No. PCT/JP2018/029820, filed on Aug. 8, 2018.

(30) Foreign Application Priority Data

Sep. 29, 2017 (JP) .............................. JP2017-191868

(51) Int. Cl.
*A61M 5/172* (2006.01)
*G16H 20/17* (2018.01)
(Continued)

(52) U.S. Cl.
CPC ........ *A61M 5/172* (2013.01); *A61M 5/31535* (2013.01); *G16H 10/65* (2018.01);
(Continued)

(58) Field of Classification Search
None
See application file for complete search history.

(56) References Cited

U.S. PATENT DOCUMENTS 5,882,338 A * 3/1999 Gray ................... A61M 5/1456
604/131
2004/0193453 A1* 9/2004 Butterfield ............. G16H 40/60
977/932
(Continued)

FOREIGN PATENT DOCUMENTS

CN 101116077 A 1/2008
CN 101304775 A 11/2008
(Continued)

OTHER PUBLICATIONS

Office Action (Notice of Reasons for Refusal) dated Jun. 7, 2022, by the Japanese Patent Office in corresponding Japanese Patent Application No. 2019-544388 and an English Translation of the Office Action. (8 pages).
(Continued)

*Primary Examiner* — Manuel A Mendez
(74) *Attorney, Agent, or Firm* — Buchanan Ingersoll & Rooney PC

(57) ABSTRACT

A medical pump includes a reader configured to read drug identification information, a storage unit that stores the drug identification information read by the reader, a notification unit, and a control unit, in which when the reader reads drug identification information anew while the drug identification information is stored in the storage unit, the control unit compares the drug identification information being stored in the storage unit with the drug identification information read anew by the reader, and when the drug identification information being stored in the storage unit does not match the drug identification information read anew by the reader, the control unit causes the notification unit to notify of non-matching between drugs.

20 Claims, 7 Drawing Sheets

(51) Int. Cl.
    *G16H 40/67*     (2018.01)
    *G16H 10/65*     (2018.01)
    *A61M 5/315*     (2006.01)

(52) U.S. Cl.
    CPC ............. *G16H 20/17* (2018.01); *G16H 40/67* (2018.01); *A61M 2205/3331* (2013.01); *A61M 2205/583* (2013.01); *A61M 2205/60* (2013.01)

(56) References Cited

U.S. PATENT DOCUMENTS

| | | |
|---|---|---|
| 2006/0229551 A1 | 10/2006 | Martinez et al. |
| 2006/0287887 A1* | 12/2006 | Hutchinson ........... A61M 5/168 705/2 |
| 2009/0156931 A1 | 6/2009 | Nemoto et al. |
| 2012/0323176 A1 | 12/2012 | Watanabe et al. |
| 2013/0261561 A1 | 10/2013 | Deberadine |
| 2015/0265763 A1 | 9/2015 | Katsunuma |
| 2015/0273143 A1 | 10/2015 | Yamada |

FOREIGN PATENT DOCUMENTS

| | | |
|---|---|---|
| CN | 102781498 A | 11/2012 |
| CN | 104922747 A | 9/2015 |
| CN | 104951644 A | 9/2015 |
| EP | 1 433 456 A1 | 6/2004 |
| JP | 2006034845 A | 2/2006 |
| JP | 2008529675 A | 8/2008 |
| JP | 2012005756 A | 1/2012 |
| JP | 2012179099 A | 9/2012 |
| JP | 2014507963 A | 4/2014 |
| WO | 03/024385 A1 | 3/2003 |
| WO | 2007/032341 A1 | 3/2007 |
| WO | 2008/004670 A1 | 1/2008 |
| WO | 2016157655 A1 | 10/2016 |

OTHER PUBLICATIONS

International Search Report (PCT/ISA/210) dated Oct. 9, 2018, by the Japan Patent Office as the International Searching Authority for International Application No. PCT/JP2018/029820.

Written Opinion (PCT/ISA/237) dated Oct. 9, 2018, by the Japan Patent Office as the International Searching Authority for International Application No. PCT/JP2018/029820.

The extended European Search Report dated Apr. 29, 2020, by the European Patent Office in corresponding European Patent Application No. 188631626-1122. (12 pages).

Office Action (The First Office Action) dated Jul. 5, 2021, by the State Intellectual Property Office of People's Republic of China in corresponding Chinese Patent Application No. 201880054883.0 and an English Translation of the Office Action. (16 pages).

\* cited by examiner

FIG. 2
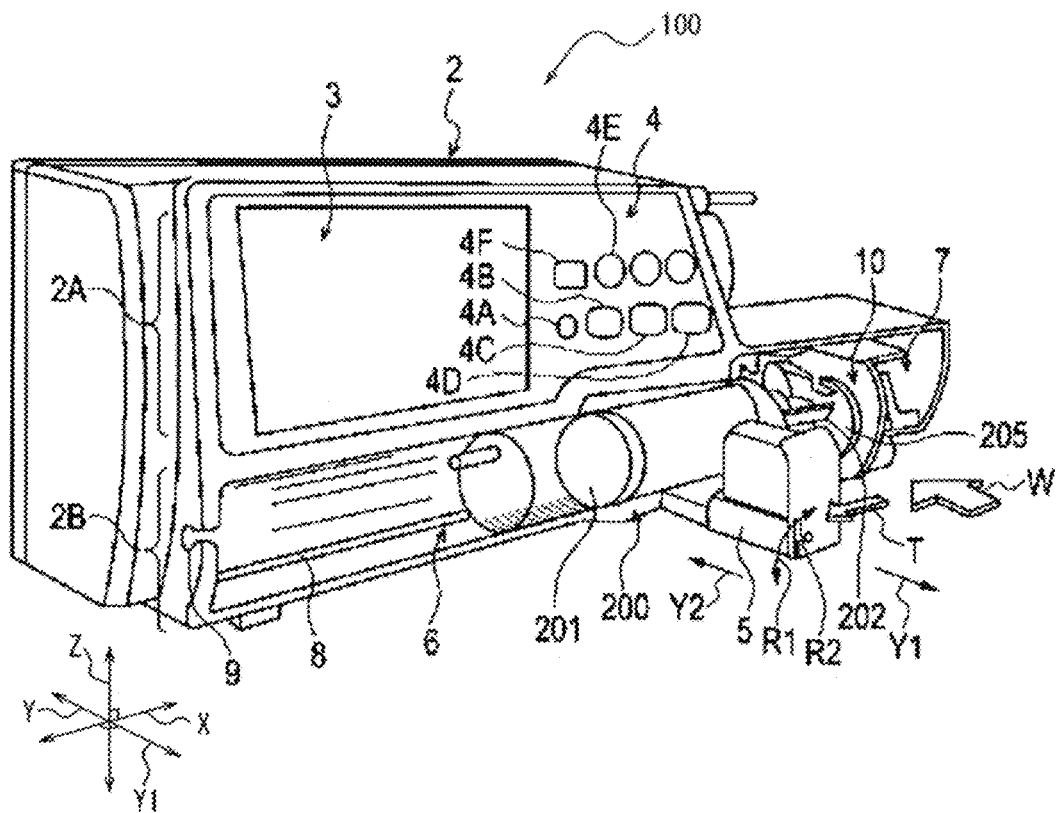
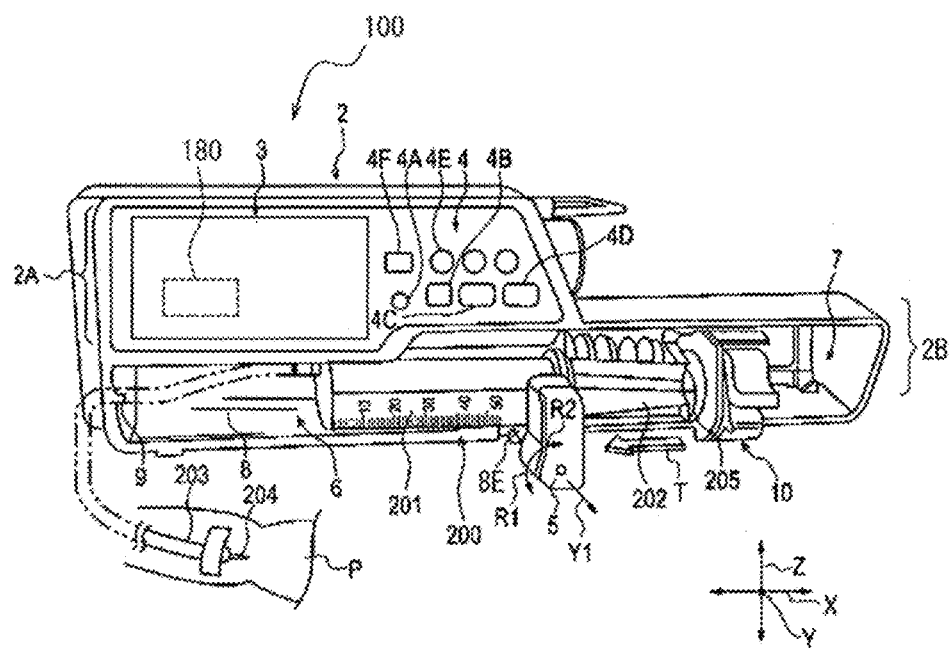
FIG. 3

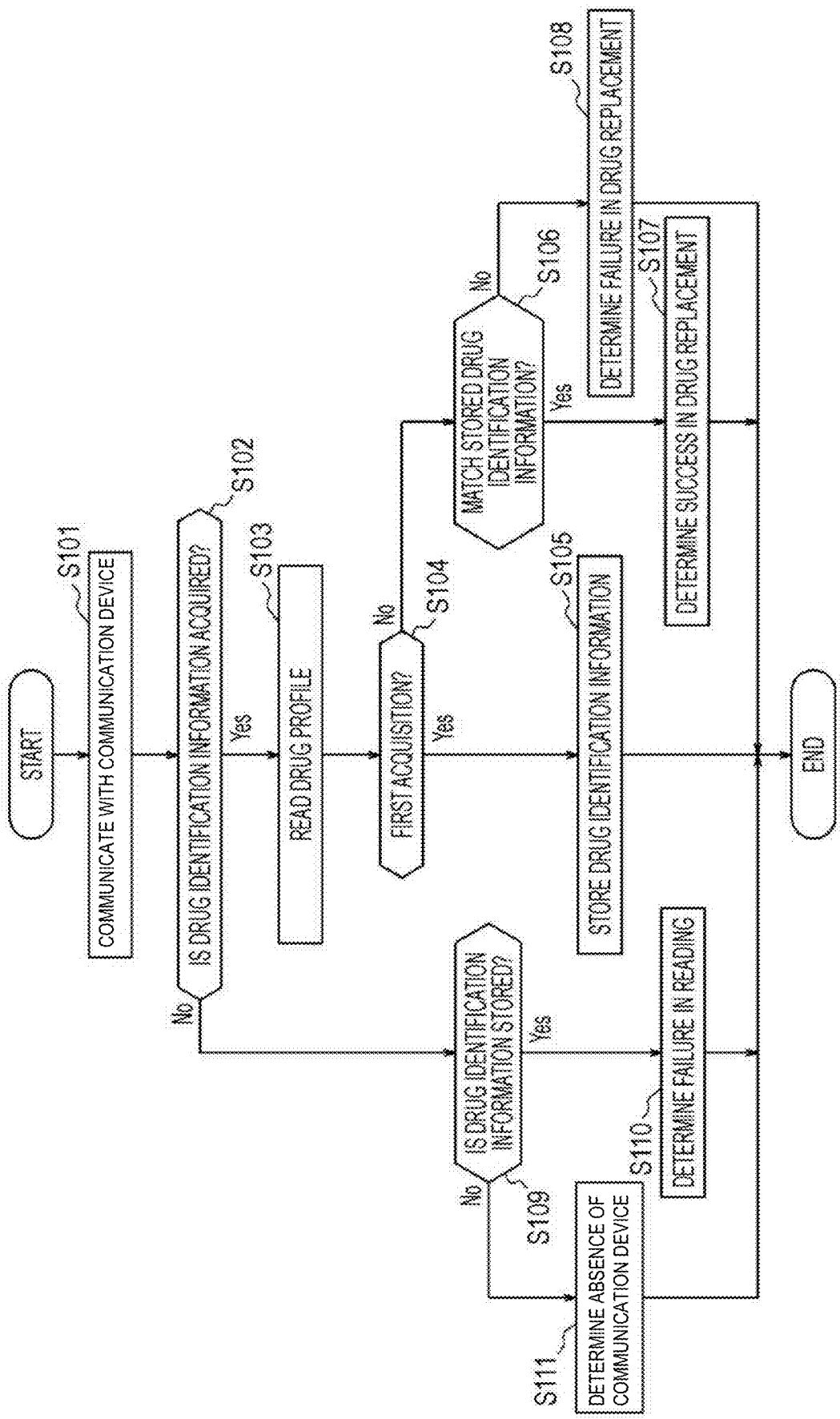

MEDICAL PUMP, METHOD OF CONTROLLING MEDICAL PUMP, AND MEDICAL PUMP SYSTEM

CROSS-REFERENCES TO RELATED APPLICATIONS

This application is a continuation of International Application No. PCT/JP2018/029820 filed on Aug. 8, 2018, which claims priority to Japanese Application No. 2017-191868 filed on Sep. 29, 2017, the entire content of both of which is incorporated herein by reference.

FIELD OF THE INVENTION

The present disclosure generally relates to a medical pump, a method of controlling a medical pump, and a medical pump system.

BACKGROUND DISCUSSION

Medical pumps, such as syringe pumps or infusion pumps, are used in, for example, operating rooms or intensive care units (ICUs). The medical pumps are used for administration of drugs, such as an anticancer agent, anesthetic, chemotherapeutic agent, and nutrient to patients for a relatively long time with high accuracy.

A technology is known to use a drug library to prevent administration of a drug with wrong setting, upon administration of a drug with a medical pump. An example is disclosed in Japanese Patent Application Publication No. 2012-179099.

The drug library is a database of setting information and the like used upon administration of, for example, each of thousands of kinds drugs. In the drug library, drugs each have setting information, such as a reference administration rate, an upper limit value/lower limit value in administration rate, a drug code, and a drug color. Hereinafter, a collection of a plurality of sets of setting information about one drug is also referred to as a "drug profile".

Various setting values of a drug profile in the drug library can be uniquely customized in a medical institution possessing a medical pump. Usually, the drug library is stored in each medical pump.

Users of the medical pumps can read drug profiles corresponding to drugs added to syringes or the like mounted on the medical pumps before setting the doses of the drugs, and thus an administration error caused by an error in setting can be reduced.

SUMMARY

When medical pumps are used to administer drugs during surgery or the like, combinations of the medical pumps and drugs are often fixed. For example, when administering a drug for a long time with a medical pump during surgery, it is sometimes necessary to replace a syringe. In such a case, the syringe is often replaced with a syringe filled with the same drug as that added to the replaced syringe.

In the medical pumps, when a used syringe is removed and replaced with a syringe filled with the same drug, a human error may occur in which the syringe is accidentally replaced with a syringe filled with another (wrong) drug.

For example, in a case where a plurality of medical pumps is used, replacement with a wrong syringe, such as the syringe having a similar drug name or similar appearance (color, shape, label, etc.), is likely to occur.

If the syringe is replaced with a wrong syringe in replacement, even if an appropriate drug is administered according to settings using the drug library before the replacement, the replacement results in an administration error after the replacement of the syringe.

Disclosed here are a medical pump, a method of controlling a medical pump, and a medical pump system that can prevent replacement of an incorrect or wrong syringe upon syringe replacement.

A medical pump according to a first aspect includes a reader configured to read drug identification information about the drugs to be administered; a storage unit that stores the drug identification information read by the reader; a notification unit; and a control unit. The control unit is configured to: compare the drug identification information stored in the storage unit with drug identification information read anew by the reader, when the reader reads the drug identification information anew while the drug identification information is stored in the storage unit; and cause the notification unit: i) to notify of non-matching between drugs when the drug identification information stored in the storage unit does not match the drug identification information read anew by the reader; and/or ii) to notify of matching between drugs when the drug identification information stored in the storage unit matches the drug identification information read anew by the reader.

As an embodiment, when the drug identification information stored in the storage unit does not match the drug identification information read anew by the reader, the control unit further causes the medical pump to be brought into a liquid feeding prohibition mode in which feeding of the drug by the medical pump is prohibited.

According to an embodiment, when the reader reads drug identification information while the drug identification information is not stored in the storage unit, the control unit causes the storage unit to store the read drug identification information in the storage unit.

In accordance with an embodiment, the reader reads the drug identification information from a syringe mounted on the medical pump.

As an embodiment, when the reader cannot read the drug identification information from a syringe mounted on the medical pump and the drug identification information is determined to be stored in the storage unit, the control unit causes the notification unit to notify of non-recognition of the drug identification information.

According to a second aspect, a medical pump is configured to receive syringes that each contain a drug to be administered to a patient, and each syringe comprises a syringe body and a syringe plunger movably positioned in the syringe body. The medical pump comprises: a syringe mounting portion configured to receive one of the syringes; a syringe plunger drive unit configured to engage and push the syringe plunger that is movably positioned in the syringe body of the syringe received at the syringe mounting portion; a reader configured to read drug identification information that is fixed to the respective syringes and that provides identifying information about the drug in each respective syringe; a storage unit that stores the drug identification information read by the reader including first syringe drug identification information which is the drug identification information on the first syringe read by the reader; a notification unit; and a control unit. The control unit is configured to: compare the first syringe drug identification information stored in the storage unit with a second syringe drug identification information on a second syringe read anew by the reader, when the reader anew reads the second syringe drug identification information while the first syringe drug identification information is stored in the storage unit; and cause the notification unit: i) to notify of non-matching between the drug in the first syringe and the drug in the second syringe when the first syringe drug identification information stored in the storage unit does not match the second syringe drug identification information read anew by the reader; and/or ii) to notify of matching between drug in the first syringe and the drug in the second syringe when the first syringe drug identification information stored in the storage unit matches the second syringe drug identification information read anew by the reader.

According to another aspect, a method of controlling a medical pump comprises: comparing the drug identification information stored in a storage unit with drug identification information read anew by the reader, when the reader anew reads the drug identification information while the drug identification information is stored in the storage unit; and notifying of non-matching between drugs, when the drug identification information stored in the storage unit does not match the drug identification information read anew by the reader and/or notifying of matching between drugs when the drug identification information stored in the storage unit matches the drug identification information read anew by the reader.

According to a further aspect, a medical pump system comprises: a medical pump configured to administer drugs; and a syringe mountable on the medical pump, wherein the syringe contains a drug. The medical pump includes: a reader configured to read drug identification information from the syringe when the syringe is mounted on the medical pump, with the drug identification information being information about the drug in the syringe; a storage unit that stores the drug identification information read by the reader; a notification unit; and a control unit. The control unit is configured to: compare the drug identification information stored in the storage unit with drug identification information read anew by the reader, when the reader anew reads the drug identification information while the drug identification information is stored in the storage unit, and cause the notification unit: i) to notify of non-matching between drugs when the drug identification information stored in the storage unit does not match the drug identification information read anew by the reader; and/or ii) to notify of matching between drugs when the drug identification information stored in the storage unit matches the drug identification information read anew by the reader.

The syringe is a prefilled syringe including a syringe body in which a drug containing an intravenous anesthetic or vasoactive agent is previously added, and a communication device is fixed to the syringe body, wherein the communication device includes a memory that stores a data set including the drug identification information corresponding to the drug added to the syringe body, and a communication unit, and the reader is configured to read the data set stored in the memory via the communication unit.

The medical pump, the method of controlling a medical pump, and the medical pump system disclosed here makes it possible to prevent wrong replacement upon syringe replacement.

BRIEF DESCRIPTION OF THE DRAWINGS

FIG. 2 is a schematic perspective view of a medical pump according to an embodiment of the present disclosure, where a syringe is mounted thereon.

FIG. 3 is a schematic front view of the medical pump illustrated in FIG. 2.

FIG. 8 is a flowchart illustrating an example of an operation of the medical pump illustrated in FIG. 1.

DETAILED DESCRIPTION

Figure 1:
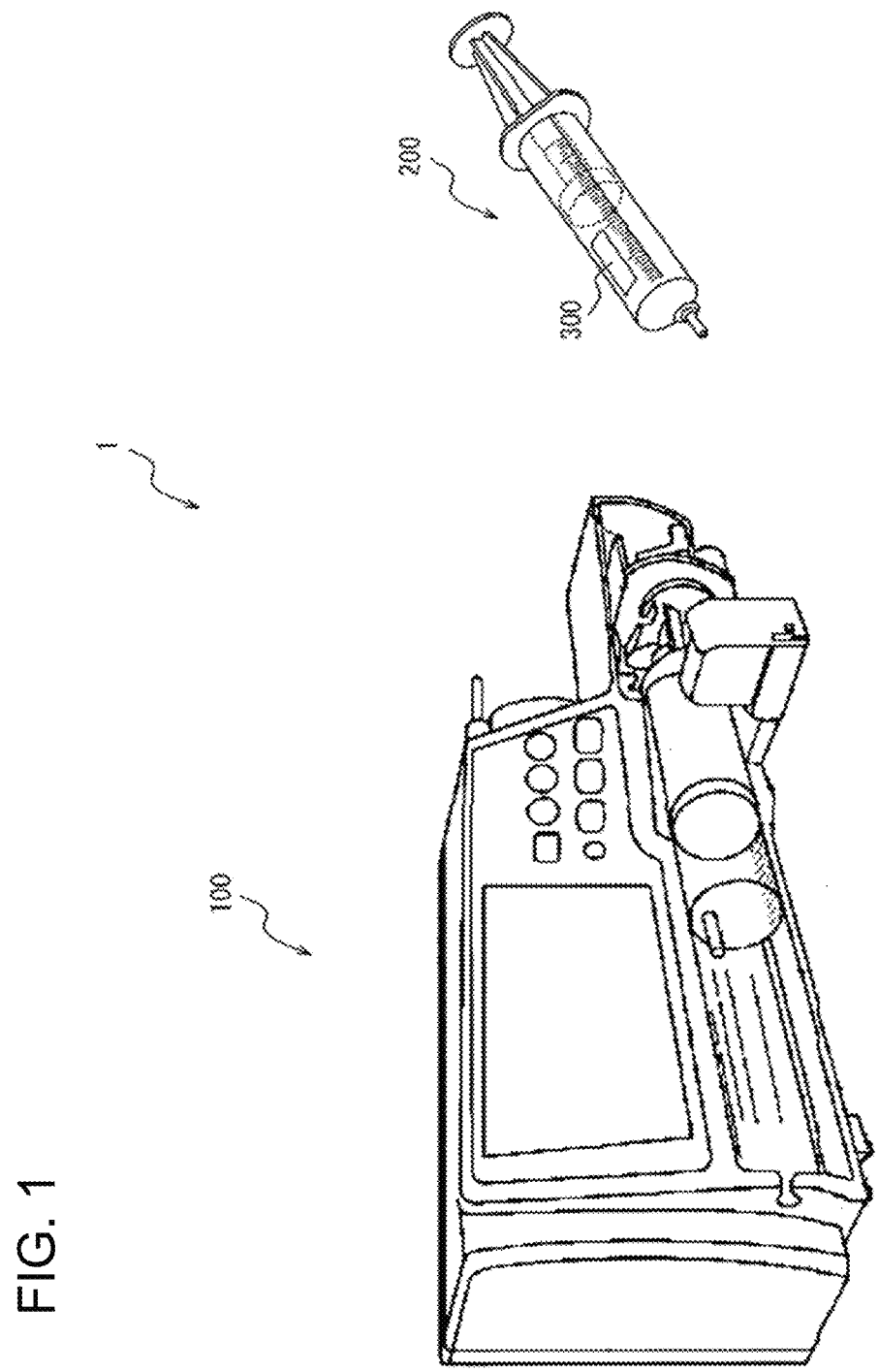
FIG. 1 is a schematic configuration view of a medical pump system according to an embodiment of the present disclosure.

Set forth below with reference to the accompanying drawings is a detailed description of embodiments of a medical pump, a method of controlling a medical pump and a medical pump system representing examples of the inventive medical pump, medical pump controlling method and medical pump system disclosed here. The dimensions or scales on the drawings may be exaggerated or different from actuality/reality for convenience of description and illustration. In the drawing figures, common features are identified by the same reference numerals.

FIG. 1 is a schematic configuration view of a medical pump system 1 according to an embodiment of the present disclosure. The medical pump system 1 includes a medical pump 100 and a syringe 200. The syringe 200 is configured to be mounted on the medical pump 100. A communication device 300 is stuck or fixed to the syringe 200.

The communication device 300 is, for example, an RFID tag. The medical pump 100 and the communication device 300 are configured to communicate with each other via short-range wireless communication, such as Near Field Communication (NFC).

Since wireless communication between the medical pump 100 and the communication device 300 has a short range, when the syringe 200 is mounted on the medical pump 100, communication between the medical pump 100 and the communication device 300 is allowed, but when the syringe 200 is away from the medical pump 100 by a predetermined distance or more, communication between the medical pump 100 and the communication device 300 is not allowed or not possible. Thus, in the medical pump 100, it is possible to prevent data from being read from the communication device 300 stuck or fixed to a syringe that is not mounted on the medical pump 100.

The communication device 300 is stuck or fixed to the syringe 200, and the communication device 300 stores a set of information (hereinafter also simply referred to as "data set") corresponding to a drug added to the syringe 200.

The medical pump 100 stores a drug library including a plurality of drug profiles.

When the syringe 200 is mounted on the medical pump 100, the medical pump 100 reads the data set stored in the communication device 300 from the communication device 300. On the basis of a drug profile corresponding to drug identification information included in the read data set, the medical pump 100 sets information about administration (hereinafter, also simply referred to as "administration information").

Here, the drug identification information is information with which a drug profile can be identified and is, for example, a drug code. Examples of the drug code include a so-called HOT reference code including a 13-digit management number, and the like.

In addition, the information about administration (administration information) includes, for example, a reference administration rate, an upper limit value/lower limit value in administration rate, and the like. The medical pump 100 is configured to set administration information corresponding to a drug added to the mounted syringe 200 to administer the drug on the basis of the administration information customized by a medical institution possessing the medical pump 100. In addition, the medical pump 100 is configured to prevent a drug from being administered at an administration rate whose value is larger than an upper limit value or lower than a lower limit value set by the medical institution possessing the medical pump 100.

Next, the medical pump 100 according to one embodiment will be described with reference to FIG. 2 and FIG. 3. FIG. 2 is a schematic perspective view of the medical pump 100 according to an embodiment of the present disclosure. FIG. 3 is a schematic front view of the medical pump 100 according to an embodiment of the present disclosure. FIGS. 2 and 3 illustrate that the medical pump 100 is a syringe pump, as an example.

The medical pump 100 is used to continuously feed a drug, such as an intravenous anesthetic, vasoactive agent, or the like added to the syringe 200 into a patient's body in an operating room, or an intensive care unit, such as an intensive care unit (ICU), a coronary care unit (CCU), and a neonatal intensive care unit (NICU). The intravenous anesthetic includes a drug that acts on the nervous system to exert a sedating effect or analgesic effect.

The medical pump 100 is configured to feed any of various drugs including intravenous anesthetics, vasoactive agents, or the like which is added to the syringe 200, into a patient's body. Examples of the applicable intravenous anesthetics include propofol, midazoram, rem ifentanil, and the like. Examples of applicable vasoactive agents include epinephrine, noradrenaline, dobutamine, dopamine, isosorbide nitrate, and nitroglycerin, and the like.

Hereinafter, an example of the configuration of the medical pump 100 will be described in detail.

As illustrated in FIG. 2 and FIG. 3, the medical pump 100 pushes a syringe plunger 202 of the syringe 200 in a T-direction to accurately feed the drug in the syringe body 201 to a patient P via a tube 203 and an indwelling needle 204, in which the syringe serves as a drug storage container filled with a drug. At this time, the syringe body 201 of the syringe 200 is set in the medical pump 100 with a clamp 5 so as not to move.

The medical pump 100 includes a main body cover 2.

The main body cover 2 is integrally molded from a resin molding material having chemical resistance. Therefore, the main body cover 2 has a splash-proof structure. The splash-proof structure can prevent intrusion of a drug or the like into the medical pump 100 even if the drug or the like is splashed on the medical pump 100. The reason why the main body cover 2 has the splash-proof structure is because a drug in the syringe body 201 may spill, an infusion solution arranged above the medical pump 100 may spill, or an antiseptic solution or the like used around the medical pump 100 may spill thereon.

As illustrated in FIGS. 2 and 3, the main body cover 2 has an upper portion 2A and a lower portion 2B.

In the upper portion 2A, a display unit 3 and an operation panel unit 4 are disposed.

In the lower portion 2B, a syringe mounting portion 6 and a syringe plunger drive unit 7 that pushes the syringe plunger 202 are arranged.

The display unit 3 is an image display device capable of color display. The display unit 3 can include, for example, a color liquid crystal display device. The display unit 3 is configured to display not only information written in Japanese but also information written in a plurality of foreign languages as required. The display unit 3 is disposed at an upper left position in the upper portion 2A of the main body cover 2 and above the syringe mounting portion 6 and the syringe plunger drive unit 7. The display unit 3 may include an input device, such as a touch sensor, to receive an input from a user.

The operation panel unit 4 is disposed on the right side of the display unit 3 in the upper portion 2A of the main body cover 2. On the operation panel unit 4, a power on/off button 4A, an operation indicator 4F, and operation buttons are arranged. FIGS. 2 and 3 each illustrate an example in which the minimum operation buttons including a fast-forward switch button 4B, a start switch button 4C, a stop switch button 4D, and a menu selection button 4E are arranged.

As illustrated in FIGS. 2 and 3, the syringe mounting portion 6 and the syringe plunger drive unit 7 are arranged side by side in an X-direction. The syringe mounting portion 6 is configured to removably fit and fix the syringe 200. The syringe mounting portion 6 is configured to fix a plurality of types of syringes 200 having different sizes.

Figure 4:
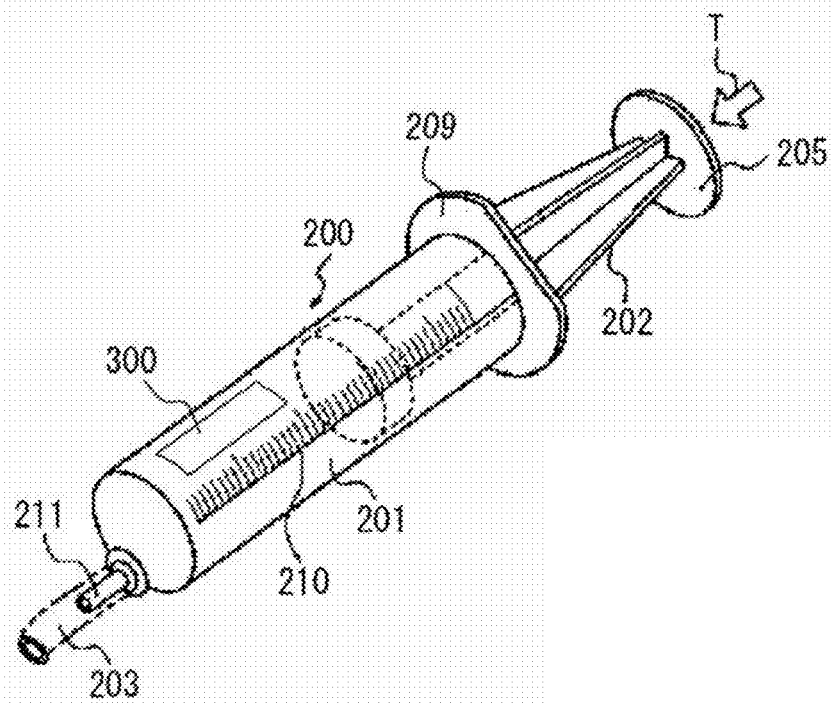
FIG. 4 is a schematic perspective view of a syringe illustrated in FIG. 1.

FIG. 4 is a perspective view of the appearance of the syringe 200. The syringe 200 includes the syringe body 201 and the syringe plunger 202. The syringe body 201 includes a main body flange 209, and the syringe plunger 202 includes a plunger flange 205. A dose scale 210 is formed on the syringe body 201. The syringe body 201 includes an outlet portion 211 to which an end portion of the tube 203, which may be a flexible tube, is removably connected. In a case where the syringe 200 is a prefilled syringe previously filled with a drug in the syringe body 201, a cap for sealing an opening portion of the outlet portion 211 is mounted to the outlet portion 211 of the syringe body 201, and the syringe 200 in such a state is provided to the medical institution. Examples of drugs to be previously added to the syringe body 201 include intravenous anesthetics, such as propofol, midazoram, and remifentanil, and vasoactive agents, such as epinephrine, noradrenaline, dobutamine, dopamine, isosorbide nitrate, and nitroglycerin.

The communication device 300 storing a data set corresponding to a drug added to the syringe 200 is stuck or fixed to the syringe body 201. In a case where the syringe 200 is a prefilled syringe, the communication device 300 having a memory storing a data set including drug identification information corresponding to the drug added to the syringe body 201 is previously stuck or fixed to the syringe body 201, and the syringe 200 in such a state is provided to the medical institution.

Figure 5:
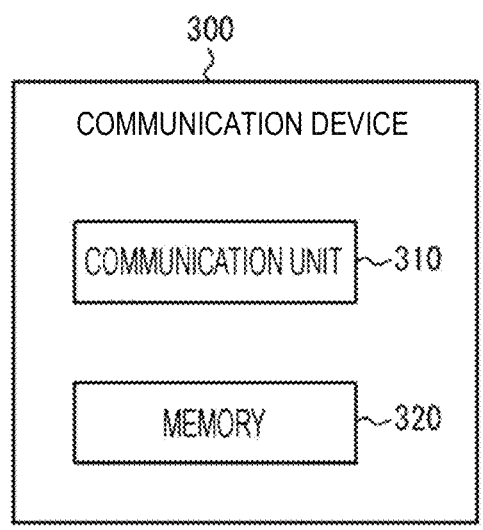
FIG. 5 is a schematic configuration diagram of a communication device illustrated in FIG. 1.

FIG. 5 is a schematic configuration diagram of the communication device 300. As described above, the communication device 300 is, for example, an RFID tag. The communication device 300 includes a communication unit 310 and a memory 320.

The communication unit 310 wirelessly communicates with a reader 170 (see FIG. 6) included in the medical pump 100. The communication unit 310 communicates with the medical pump 100 via short-range wireless communication, such as NFC.

The memory 320 stores information such as a data set corresponding to a drug added to the syringe 200. The data set stored in the memory 320 includes drug identification information such as a drug code. The data set stored in the memory 320 may further include a drug profile.

When receiving a data-set transmission request from the medical pump 100, the communication unit 310 transmits the data set stored in the memory 320 to the medical pump 100.

A configuration of the medical pump 100 will be described with reference to FIGS. 2 and 3 again.

The syringe mounting portion 6 includes a housing portion 8 that houses the syringe body 201, and the clamp 5. In order to house the syringe body 201, the housing portion 8 has a recess portion having a substantially semicircular cross-section and extending in an X-direction. The housing portion 8 has a wall portion at an end, and the wall portion includes a tube fixing portion 9 that removably holds the tube 203.

To remove the syringe 200 from the syringe mounting portion 6 by operating the clamp 5, the clamp 5 is pulled in a Y1-direction (frontward) against the force of a spring (not illustrated) and further turned 90 degrees in an R1-direction. This operation releases the fixation of the syringe body 201 by the clamp 5, and the syringe 200 can be removed from the housing portion 8. Furthermore, to mount the syringe 200 to the syringe mounting portion 6 by operating the clamp 5, the clamp 5 is pulled in a Y1-direction against the force of the spring (not illustrated) and further turned 90 degrees in an R2-direction to be returned in a Y2-direction by the spring force. With this operation, the syringe body 201 can be housed in the housing portion 8, and the syringe body 201 can be fixed by the clamp 5. A right end portion 8E of the housing portion 8 of the syringe mounting portion 6 is partially cut away so that the clamp 5 may fix syringes 200 having various/different capacities, such as 5 mL, 10 mL, 20 mL, 30 mL, and 50 mL.

When the syringe body 201 is housed and fixed in the housing portion 8, the syringe plunger 202 is arranged in the syringe plunger drive unit 7. The syringe plunger drive unit 7 includes a slider 10. This slider 10 pushes the plunger flange 205 of the syringe plunger 202 little by little in a T-direction relative to the syringe body 201 in response to a command from a control unit 180 illustrated in FIG. 3.

The X-direction, the Y-direction, and the Z-direction in FIGS. 2 and 3 are orthogonal to each other, and the Z-direction represents a vertical direction.

Next, an example of an electrical configuration of the medical pump 100 illustrated in FIG. 1 will be described in detail with reference to FIG. 6

Figure 6:
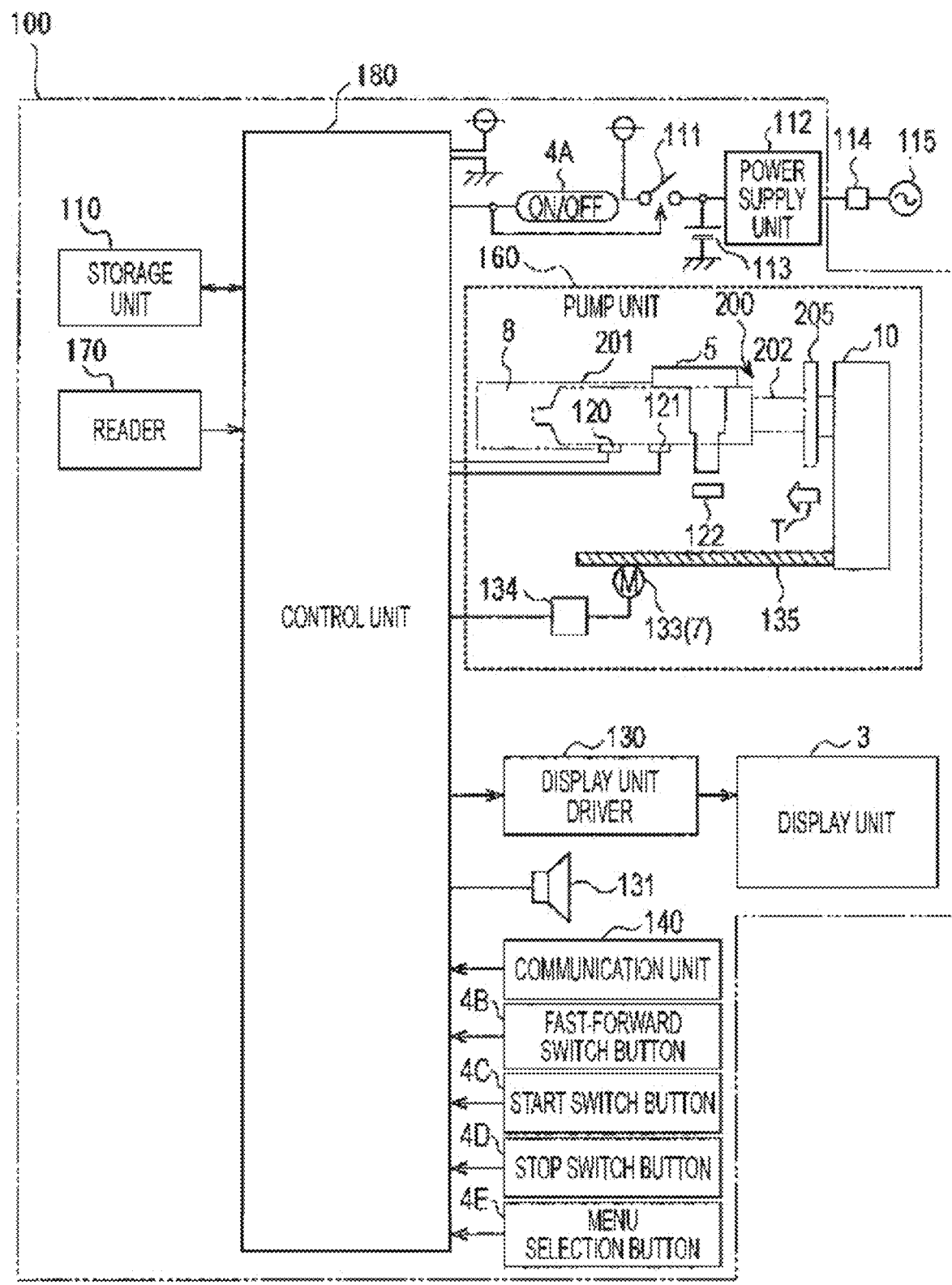
FIG. 6 is a schematic diagram illustrating an electrical configuration of the medical pump illustrated in FIG. 1.

In FIG. 6, the medical pump 100 includes the control unit (computer) 180 that performs determination and control of the overall operation. The control unit 180 is, for example, a one-chip microcomputer.

The power on/off button 4A and a switch 111 are connected to the control unit 180.

The switch 111 switches between a power converter unit (power supply unit) 112 and a rechargeable battery 113, such as a lithium-ion battery, to supply power from one of the power converter unit 112 or the rechargeable battery 113 to the control unit 180.

The power converter unit 112 is connected to a commercial AC power supply 115 via an outlet 114.

In FIG. 6, a pump unit 160 is electrically connected to the control unit 180. The pump unit 160 administers a drug to the patient according to administration information set on the basis of a drug profile, in response to a command from the control unit 180.

In FIG. 6, in the housing portion 8 of the pump unit 160, a pair of detection switches 120 and 121 is arranged. The detection switches 120 and 121 detect whether the syringe body 201 of the syringe 200 is correctly arranged in the housing portion 8, and notify the control unit 180 of such a detection.

The pump unit 160 includes a clamp sensor 122 that detects a positional state of the clamp 5 to notify the control unit 180 whether the syringe body 201 is securely clamped.

The syringe plunger drive unit 7 of the pump unit 160 includes a motor 133, and when the motor 133 is driven by a motor driver 134 in response to a command from the control unit 180, the motor 133 turns a lead screw 135 to move the slider 10 in a T-direction. Therefore, the slider 10 presses the plunger flange 205 of the syringe plunger 202 in the T-direction and accurately feeds a drug in the syringe body 201 illustrated in FIG. 3 to the patient P through the tube 203 and the indwelling needle 204.

In FIG. 6, the fast-forward delivery switch button 4B, the start switch button 4C, the stop switch button 4D, and the menu selection button 4E are electrically connected to the control unit 180. When the start switch button 4C is pressed, a liquid feeding start control signal is input to the control unit 180. Furthermore, when the stop switch button 4D is pressed, a liquid feeding stop control signal is input to the control unit 180.

In FIG. 6, a display unit driver 130 is electrically connected to the control unit 180. The display unit driver 130 drives the display unit 3 in response to a command from the control unit 180 and displays various information on the display unit 3.

In FIG. 6, a notification unit 131 is electrically connected to the control unit 180. The notification unit 131 notifies of various alarm contents by voice, light, vibration, or the like in response to a command from the control unit 180. Furthermore, in a case where the control unit 180 notifies of various alarm contents by display on the display unit 3, the display unit 3 may have a function as a notification unit.

The communication unit 140 transmits/receives data to/from a server or the like of a medical institution via a network. Furthermore, the communication unit 140 may be connected locally to a computer, such as a desktop computer, to transmit/receive data.

The reader 170 communicates with the communication unit 310 of the communication device 300 stuck or fixed to the syringe 200 via short-range wireless communication, such as NFC.

When the syringe 200 is mounted on the medical pump 100, the reader 170 transmits a data-set transmission request including drug identification information to the communication device 300. The reader 170 reads the data set transmitted from the communication device 300 in response to the transmission request from the reader 170.

The storage unit 110 may include, for example, a semiconductor memory, a magnetic memory, or the like. The storage unit 110 stores various information and programs necessary for the operation of the medical pump 100.

The storage unit 110 stores a drug library including a plurality of drug profiles. The storage unit 110 is configured to store a drug library customized by the medical institution possessing the medical pump 100. For example, download of a drug library stored in a server of a medical institution to the storage unit 110 via the communication unit 140 by the control unit 180 enables the storage unit 110 to store the drug library customized by the medical institution.

When the syringe 200 is mounted on the medical pump 100 and the reader 170 reads a data set from the communication device 300, the control unit 180 acquires drug identification information included in the data set. The drug identification information is, for example, a drug code but is not limited to the drug code, and may preferably be information that can specify a drug.

The control unit 180 reads, from the storage unit 110, a drug profile corresponding to the acquired drug identification information. The control unit 180 sets administration information or the like on the basis of information of the drug profile read from the storage unit 110. As described above, the administration information includes a reference administration rate, an upper limit value/lower limit value in administration rate, and the like.

When the drug profile corresponding to the acquired drug identification information is not included in the storage unit 110, and if the drug profile corresponding to the drug identification information is included in the data set read by the reader 170, the control unit 180 may acquire the drug profile included in the data set. In this case, the control unit 180 sets the administration information or the like on the basis of the information of the drug profile acquired from the data set read by the reader 170.

When reading a drug profile corresponding to a drug added to the syringe 200 mounted on the medical pump 100, the control unit 180 causes information included in the drug profile to be reflected to update display contents of the display unit 3.

Figure 7:
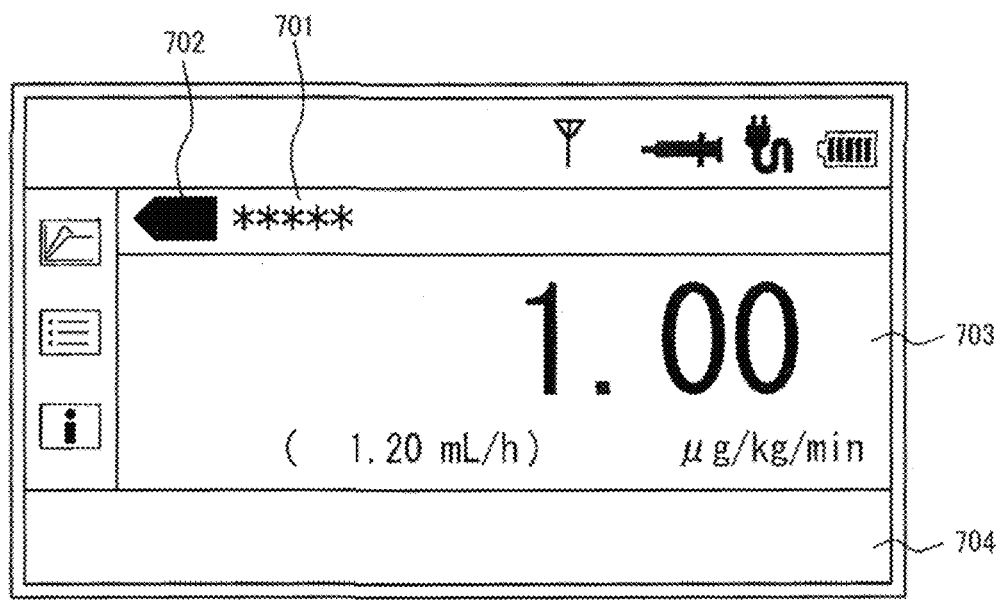
FIG. 7 is an example of display on a display unit of the medical pump illustrated in FIG. 1.

FIG. 7 illustrates an example of display on the display unit 3 in response to reading a drug profile by the control unit 180. In the example illustrated in FIG. 7, a drug name display field 701, a drug color display field 702, and an administration setting display field 703 are displayed. Furthermore, when there is a message, the message is displayed in a message field 704.

In the drug name display field 701, a drug name, such as "nitroglycerin", is displayed. In the drug color display field 702, a color previously set corresponding to a drug is displayed.

In the administration setting display field 703, for example, a reference administration rate, a reference flow rate, and the like are displayed. In the example illustrated in FIG. 7, 1.00 [μg/kg/min] is displayed as the reference administration rate, and 1.20 [mL/h] is displayed as the reference flow rate. The user can change, for example, the reference administration rate as required. However, when a value set by the user exceeds an upper limit value of an administration rate defined in the drug profile or falls below a lower limit value thereof, the control unit 180 causes the notification unit 131 to give a warning. In a case where the display unit 3 functions as the notification unit, the control unit 180 may change the display on the display unit 3 to give a warning. Thereby, the medical pump 100 is operable to prevent the user from administering a drug at an administration rate larger than the upper limit value of an administration rate defined in the drug profile or smaller than the lower limit value thereof.

In the message field 704, a message, such as "drug is recognized", is displayed in response to reading a drug profile by the control unit 180.

When the start switch button 4C is pressed, the control unit 180 controls the pump unit 160 to feed a drug to a patient according to set administration information.

The control unit 180 causes the storage unit 110 to store drug identification information corresponding to a drug being used, as "in-use drug identification information".

When acquiring drug identification information from a data set read by the reader 170 while the in-use drug identification information is not stored in the storage unit 110, the control unit 180 causes the storage unit 110 to store the drug identification information as the in-use drug identification information. For example, when acquiring first drug identification information after the power on/off button 4A is pressed to turn on power of the medical pump 100, the control unit 180 causes the storage unit 110 to store the drug identification information as the in-use drug identification information. More specifically, the control unit 180 acquires first drug identification information after the power on/off button 4A is pressed to turn on the medical pump 100 and causes the storage unit 110 to store the drug identification information as the in-use drug identification information, in conjunction with pressing the start switch button 4C to start liquid feeding. Thereby, the control unit 180 is operable to cause the storage unit 110 to store only drug identification information corresponding to a drug actually being fed, as the in-use drug identification information. In addition, in conjunction with first acquisition of drug identification information after the power on/off button 4A is pressed to turn on power of the medical pump 100, the control unit 180 may cause the storage unit 110 to store the drug identification information as the in-use drug identification information.

When acquiring drug identification information from a new data set that is read by the reader 170 while the in-use drug identification information is stored in the storage unit 110, the control unit 180 compares the in-use drug identification information stored in the storage unit 110 with the drug identification information acquired anew.

When the in-use drug identification information does not match the drug identification information acquired anew, the control unit 180 causes the notification unit 131 or the display unit 3 to give a warning that a drug added to a new syringe 200 mounted on the medical pump 100 does not match a drug added to a syringe 200 mounted on the medical pump 100 before replacement. In a case where the display unit 3 is caused to function as the notification unit, the control unit 180 causes, for example, the message field 704 of the display unit 3 illustrated in FIG. 7 to display a message "different drug is recognized." Thereby, the medical pump 100 is operable to prevent the user from replacing a syringe 200 with a syringe 200 filled with a wrong drug.

When the in-use drug identification information does not match the drug identification information acquired anew, the control unit 180 may further cause the medical pump 100 to be brought into a liquid feeding prohibition mode. Here, the "liquid feeding prohibition mode" is a mode in which liquid feeding is not started even if the start switch button 4C is pressed by the user. In the liquid feeding prohibition mode, the control unit 180 may cause the notification unit 131 to notify of the liquid feeding prohibition by a voice or the like when the start switch button 4C is pressed. These processes enable the medical pump 100 to more accurately prevent start to feed a wrong drug upon replacement with a syringe 200 filled with the wrong drug.

The user often replaces a syringe 200 with a syringe 200 filled with the same drug as a drug added to the syringe 200 before replacement, but the user sometimes intentionally replaces the syringe 200 with a syringe filled with a different drug. Therefore, the control unit 180 may shift the liquid feeding prohibition mode to a liquid feeding permission mode by a user's predetermined operation.

For example, when the user operates the medical pump 100 to manually change the setting of a dosage unit, the control unit 180 causes the medical pump 100 to be brought into the liquid feeding permission mode from the liquid feeding prohibition mode.

The dosage unit includes mL/h which is set according to how much drug is fed per unit time, μg/kg/min and μg/kg/h which is set according to how much drug is administered per unit time on the basis of a drug concentration and a patient's body weight, and the like.

Furthermore, for example, when the user manually changes a drug profile by operating the medical pump 100, the control unit 180 causes the medical pump 100 to be brought into the liquid feeding permission mode from the liquid feeding prohibition mode.

Manual change of setting, such as a dosage unit or drug profile by the user is considered that the user intentionally changes the setting to be suitable for a drug after replacement. Therefore, when the user manually changes the setting, such as a dosage unit or drug profile, the control unit 180 causes the medical pump 100 to be brought into the liquid feeding permission mode from the liquid feeding prohibition mode. When the mode is shifted to the liquid feeding permission mode, the medical pump 100 is allowed to start liquid feeding when the start switch button 4C is pressed.

Furthermore, since the in-use drug identification information is stored in the storage unit 110, when the control unit 180 causes the medical pump 100 to be brought into the liquid feeding prohibition mode and, for example, the user presses the power on/off button 4A to turn off the power of the medical pump 100, the control unit 180 deletes the in-use drug identification information stored in the storage unit 110. Therefore, when the user presses the power on/off button 4A again to turn on the power of the medical pump 100, the state of the liquid feeding prohibition mode has been canceled. In order to facilitate the shift from the liquid feeding prohibition mode to the liquid feeding permission mode, for example, the control unit 180 may cancel the state of the liquid feeding prohibition mode by pressing the start switch button 4C and/or the stop switch button 4D for a predetermined time period.

Furthermore, as described above, also when the user manually changes the setting, such as a dosage unit or a drug profile, the control unit 180 may delete the in-use drug identification information stored in the storage unit 110.

When the in-use drug identification information matches the drug identification information acquired anew, the control unit 180 may cause the notification unit 131 or the display unit 3 to notify that a drug added to a new syringe 200 mounted on the medical pump 100 matches a drug added to a syringe 200 mounted on the medical pump 100 before replacement. In a case where the display unit 3 is caused to function as the notification unit, the control unit 180 causes, for example, the message field 704 of the display unit 3 illustrated in FIG. 7 to display a message "the same drug is recognized."

In the present embodiment, it is assumed that when the in-use drug identification information does not match the drug identification information acquired anew, the control unit 180 causes the notification unit 131 or the display unit 3 to notify of the non-matching. However, the control unit 180 may be configured so that when the in-use drug identification information does not match the drug identification information acquired anew, the notification unit 131 or the display unit 3 is caused not to notify of the non-matching, and when the in-use drug identification information matches the drug identification information acquired anew, the notification unit 131 or the display unit 3 is caused to notify of the matching.

The medical pump 100 may have a mode (hereinafter, also referred to as "wrong-drug detection invalidation mode") in which whether the in-use drug identification information matches the drug identification information acquired anew is not determined. When the user sets the wrong-drug detection invalidation mode, the control unit 180 does not determine whether the in-use drug identification information matches the drug identification information acquired anew. Such a wrong-drug detection invalidation mode can reduce the user's trouble due to warning notification in a case where a drug is often replaced with a different drug. Furthermore, in a case where the wrong-drug detection invalidation mode is set, the control unit 180 may overwrite the in-use drug identification information with the drug identification information when the drug identification information is acquired.

Furthermore, in the above-described wrong-drug detection invalidation mode, the control unit 180 determines whether the in-use drug identification information matches the drug identification information acquired anew, but the wrong-drug detection invalidation mode is not caused to be shifted to the liquid feeding prohibition mode. In this case, after determining whether the in-use drug identification information matches the drug identification information acquired anew, the control unit 180 may overwrite the in-use drug identification information with the drug identification information acquired anew.

An example of an operation of the medical pump 100 will be described with reference to a flowchart illustrated in FIG. 8.

When a syringe 200 is mounted on the medical pump 100, the reader 170 of the medical pump 100 starts communication with a communication device 300 (step S101).

The control unit 180 determines whether drug identification information has been acquired from the communication device 300 (step S102).

If the drug identification information has been acquired from the communication device 300 (Yes in step S102), the control unit 180 reads a drug profile corresponding to the acquired drug identification information, from the storage unit 110 (step S103).

The control unit 180 determines whether in-use drug identification information is stored in the storage unit 110, that is, whether the drug identification information is acquired for the first time (step S104).

If the drug identification information is acquired for the first time (Yes in step S104), the control unit 180 causes the storage unit 110 to store the acquired drug identification information as the in-use drug identification information (step S105).

If it is not the first time to acquire the drug identification information (No in step S104), the control unit 180 determines whether the in-use drug identification information stored in the storage unit 110 matches the drug identification information acquired anew (step S106).

If the in-use drug identification information stored in the storage unit 110 matches the drug identification information acquired anew (Yes in step S106), the control unit 180 determines that drug replacement has succeeded and causes the notification unit 131 or the display unit 3 to notify of matching between the drugs before and after replacement (step S107).

If the in-use drug identification information stored in the storage unit 110 does not match the drug identification information acquired anew (No in step S106), the control unit 180 determines that drug replacement has failed and causes the notification unit 131 or the display unit 3 to notify that the drug before replacement does not match the drug after replacement (step S108).

In step S102, for example, if it is determined that the reader 170 cannot communicate with the communication device 300 and the drug identification information cannot be acquired from the communication device 300 (No in step S102), the control unit 180 determines whether the in-use drug identification information is stored in the storage unit 110 (step S109).

If the in-use drug identification information is stored in the storage unit 110 (Yes in step S109), the control unit 180 determines that reading of the drug identification information from the communication device 300 has failed due to a communication failure or the like (step S110). The reason why drug identification information cannot be acquired after replacement of a syringe 200 even though the drug identification information can be acquired before the replacement thereof is because there is a high possibility of a communication failure between the reader 170 and the communication device 300. At this time, the control unit 180 may cause, for example, the message field 704 (see FIG. 7) of the display unit 3, functioning as a notification unit, to display a message of non-recognition of the drug identification information, for example, "Tag cannot be recognized. Please confirm the position." Furthermore, the control unit 180 may further cause the medical pump 100 to be brought into the liquid feeding prohibition mode.

If the in-use drug identification information is not stored in the storage unit 110 (No in step S109), the control unit 180 determines that the communication device 300 is not stuck or fixed to any of a syringe 200 before replacement and a syringe 200 after replacement (step S111). In this case, the control unit 180 allows the user to make a determination of whether the syringes 200 before and after replacement match each other, and does not cause the medical pump 100 to be brought into the liquid feeding prohibition mode. That is, the liquid feeding permission mode is maintained.

The control unit 180 may execute determination processing of step S106 after the start switch button 4C is pressed at the liquid feeding permission mode. In this state, when the user who noticed that a wrong syringe 200 has been mounted before starting liquid feeding removes the syringe 200, upon replacement of the syringe 200, the control unit 180 does not cause the notification unit 131 or the display unit 3 to notify of a warning, even if drugs added to the syringes 200 before and after replacement do not match each other. Specifically, when the start switch button 4C is pressed, the control unit 180 executes the determination processing of step S106. If the in-use drug identification information stored in the storage unit 110 does not match the drug identification information acquired anew (No in step S106), the control unit 180 determines that the drug replacement has failed, causes the notification unit 131 or the display unit 3 to notify of non-match of the drugs before and after the replacement (step S108), and does not cause liquid feeding to start.

On the other hand, when the in-use drug identification information stored in the storage unit 110 matches the drug identification information acquired anew (Yes in step S106), the control unit 180 determines that the drug replacement has succeeded, causes the notification unit 131 or the display unit 3 to notify of matching between the drugs before and after replacement (step S107), and causes the liquid feeding to start.

In addition, the control unit 180 may execute determination processing of step S104 after the start switch button 4C is pressed at the liquid feeding permission mode. Specifically, when the start switch button 4C is pressed, the control unit 180 executes the determination processing of step S104. If the drug identification information is acquired for the first time (Yes in step S104), the control unit 180 causes the storage unit 110 to store the acquired drug identification information as the in-use drug identification information (step S105) and causes the liquid feeding to start. If it is not the first time to acquire the drug identification information (No in step S104), the control unit 180 does not start liquid feeding and executes the determination processing of step S106 described above.

As described above, in the medical pump 100 disclosed here, when the reader 170 reads drug identification information anew while the drug identification information is stored in the storage unit 110, the control unit 180 compares the drug identification information stored in the storage unit 110 with the drug identification information read anew by the reader 170, and when the drug identification information being stored in the storage unit 110 does not match the drug identification information read anew by the reader 170, the control unit 180 causes the notification unit 131 or the display unit 3 to notify of the non-matching between drugs. Thereby, the medical pump 100 disclosed here is operable to prevent wrong replacement upon replacement of a syringe 200.

Furthermore, in the present embodiment, when the drug identification information stored in the storage unit 110 does not match the drug identification information read anew by the reader 170, the control unit 180 may further cause the medical pump 100 to be brought into the liquid feeding prohibition mode. Thereby, the medical pump 100 is operable to prevent the start of liquid feeding upon replacement with a wrong syringe 200.

The present invention is not limited to the embodiments described above, and various alterations and modifications may be made by those skilled in the art within the technical scope of the present invention. For example, the medical pump is not limited to a syringe pump and may be another type of medical pump, such as an infusion pump that delivers a drug stored in an infusion bag.

Furthermore, instead of the communication device 300, a graphic having information, such as a barcode or a QR code (registered trademark), may be stuck to the syringe 200. In this case, the bar code or QR code includes the drug identification information, and the reader 170 of the medical pump 100 reads the drug identification information from the bar code or QR code.

The present disclosure relates to a medical pump, a method of controlling a medical pump, and a medical pump system and thus has industrial applicability.

The detailed description above describes embodiments of a medical pump, a method of controlling a medical pump and a medical pump system representing examples of the inventive medical pump, medical pump controlling method and medical pump system disclosed here. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A medical pump configured to administer drugs comprising:
   a housing configured to receive a first drug storage container containing a drug to be administered, the housing also being configured to receive, after the first drug storage container is removed from the housing, a second drug storage container containing a drug to be administered;
   a reader configured to read drug identification information about the drug in the first drug storage container when the first drug storage container is received in the housing and configured to read drug identification information about the drug in the second drug storage container when the second drug storage container is received in the housing;
   a storage unit that stores the drug identification information read by the reader about the drug in the first drug storage container;
   a notification unit; and
   a control unit,
   the control unit being configured to:
      compare the drug identification information stored in the storage unit about the drug in the first drug storage container with the drug identification information read by the reader about the drug in the second drug storage container; and
      cause the notification unit: i) to notify of non-matching drugs when the control unit determines, based on the compare, that the drug identification information stored in the storage unit about the drug in the first drug storage container does not match the drug identification information read by the reader about the drug in the second drug storage container; and/or ii) to notify of matching drugs when the control unit determines, based on the compare, that the drug identification information stored in the storage unit about the drug in the first drug storage container matches the drug identification information read by the reader about the drug in the second drug storage container.

2. The medical pump according to claim 1, wherein when the drug identification information stored in the storage unit about the drug in the first drug storage container does not match the drug identification information read by the reader about the drug in the second drug storage container, the control unit further causes the medical pump to be brought into a liquid feeding prohibition mode in which the medical pump is prohibited from feeding the drug in the second drug storage container when the second drug storage container is received in the housing.

3. The medical pump according to claim 1, wherein when the reader reads the drug identification information about the drug in the first drug storage container, the control unit causes the storage unit to store the read drug identification information about the drug in the first drug storage container in the storage unit.

4. The medical pump according to claim 1, wherein the reader: i) reads the drug identification information about the drug in the first drug storage container from a communication device on the first drug storage container; and reads the drug identification information about the drug in the second drug storage container from a communication device on the second drug storage container.

5. The medical pump according to claim 4, wherein when the reader cannot read the drug identification information about the drug in the second drug storage container from the communication device on the second drug storage container and the drug identification information about the drug in the first drug storage container is determined to be stored in the storage unit, the control unit causes the notification unit to notify of non-recognition of the drug identification information about the drug in the second drug storage container.

6. A medical pump configured to receive syringes that each contain a drug to be administered to a patient, each syringe comprising a syringe body and a syringe plunger movably positioned in the syringe body, the medical pump comprising:
   a syringe mounting portion configured to receive one of the syringes;
   a syringe plunger drive unit configured to engage and push the syringe plunger that is movably positioned in the syringe body of the syringe received at the syringe mounting portion;
   a reader configured to read drug identification information that is fixed to the respective syringes and that provides identifying information about the drug in each respective syringe;
   a storage unit that stores the drug identification information read by the reader including first syringe drug identification information which is the drug identification information on the first syringe read by the reader;
   a notification unit; and
   a control unit,
   the control unit being configured to:
      compare the first syringe drug identification information stored in the storage unit with a second syringe drug identification information on a second syringe read anew by the reader, when the reader anew reads the second syringe drug identification information while the first syringe drug identification information is stored in the storage unit; and
      cause the notification unit: i) to notify of non-matching between the drug in the first syringe and the drug in the second syringe when the first syringe drug identification information stored in the storage unit does not match the second syringe drug identification information read anew by the reader; and/or ii) to notify of matching between drug in the first syringe and the drug in the second syringe when the first syringe drug identification information stored in the storage unit matches the second syringe drug identification information read anew by the reader.

7. The medical pump according to claim 6, wherein when the first syringe drug identification information stored in the storage unit does not match the second syringe drug identification information read anew by the reader, the control unit further causes the medical pump to be brought into a liquid feeding prohibition mode in which feeding of the drug in the second syringe by the medical pump is prohibited .

8. The medical pump according to claim 7, wherein the control unit further causes the medical pump, when in the liquid feeding prohibition mode, to be brought into a liquid feeding permission mode, when a setting of the medical pump is manually changed by a user, in which feeding of the drug in the second syringe by the medical pump is permitted.

9. The medical pump according to claim 6, wherein the notification unit is a display that notifies of the matching and/or the non-matching by a notification on the display.

10. A method of controlling a medical pump, the medical pump including: i) a housing configured to receive drug storage containers, including first and second drug storage containers each containing a respective drug to be administered and each including respective drug identification information identifying information about the drug in the respective drug storage container; ii) a reader configured to read the drug identification information; and iii) a storage unit in which is stored the drug identification information read by the reader about the drug in the first drug storage container, the method comprising:

comparing the drug identification information stored in the storage unit about the drug in the first drug storage container with the drug identification information read by the reader about the drug in the second drug storage container; and notifying of non-matching drugs, when the drug identification information stored in the storage unit about the drug in the first drug storage container does not match the drug identification information read by the reader about the drug in the second drug storage container and/or notifying of matching drugs when the drug identification information stored in the storage unit about the drug in the first drug storage container matches the drug identification information read by the reader about the drug in the second drug storage container.

11. The method according to claim 10, wherein the second drug storage container is mounted on the medical pump during the comparing of the drug identification information stored in the storage unit about the drug in the first drug storage container with the drug identification information read by the reader about the drug in the second drug storage container, the method further comprising prohibiting the medical pump from expelling drug in the second drug storage container when the drug identification information stored in the storage unit about the drug in the first drug storage container does not match the drug identification information read by the reader about the drug in the second drug storage container.

12. The method according to claim 11, wherein the second drug storage container mounted on the medical pump comprises a syringe body and a syringe plunger movably positioned in the syringe body, and wherein the prohibiting of the medical pump from expelling drug in the one syringe comprises prohibiting the plunger from being moved forward in the syringe body.

13. The method according to claim 11, wherein following the medical pump being prohibited from expelling drug in the second drug storage container, permitting the medical pump to expel the drug in the second drug storage container when a setting of the medical pump is manually changed by a user.

14. The method according to claim 10, wherein the notifying includes notifying on a display.

15. The method according to claim 10, wherein when the reader reads the drug identification information about the drug in the first drug storage container while the first drug storage container is received in the housing, the control unit causes the storage unit to store the read drug identification information about the drug in the first drug storage container in the storage unit.

16. The method according to claim 10, wherein the drug identification information read by the reader about the drug in the second drug storage container is read while the second drug storage container is received in the housing off the medical pump.

17. The method according to claim 16, further comprising notifying of non-recognition of the drug identification information about the drug in the second drug storage container when the reader cannot read the drug identification information about the drug in the second drug storage container from the second drug storage container received in the housing while the drug identification information about the drug in the first drug storage container is determined to be stored in the storage unit.

18. A medical pump system comprising:
a medical pump configured to administer drugs; and
a first syringe mountable on the medical pump, the first syringe containing a drug, the first syringe being removable from the medical pump so that a second syringe containing a drug is mountable on the medical pump;
the medical pump including:
a reader configured to read first drug identification information from the first syringe when the first syringe is mounted on the medical pump and to read second drug identification information from the second syringe when the second syringe is mounted on the medical pump, the first drug identification information being information about the drug in the first syringe, the second drug identification information being information about the drug in the second syringe;
a storage unit that stores the first drug identification information read by the reader;
a notification unit; and
a control unit,
the control unit being configured to:
compare the first drug identification information stored in the storage unit with the second drug identification information read by the reader, when the reader reads the second drug identification information while the first drug identification information is stored in the storage unit, and
cause the notification unit: i) to notify of non-matching drugs when the first drug identification information stored in the storage unit does not match the second drug identification information read by the reader; and/or ii) to notify of matching drugs when the first drug identification information stored in the storage unit matches the second drug identification information read by the reader.

19. The medical pump system according to claim 18, wherein
the first syringe is a prefilled syringe including a syringe body in which a drug containing an intravenous anesthetic or vasoactive agent is previously added, and a communication device fixed to the syringe body,
the communication device includes a memory that stores a data set including the first drug identification information corresponding to the drug added to the syringe body, and a communication unit, and
the reader is configured to read the data set stored in the memory via the communication unit.

20. The medical pump system according to claim 19, wherein when the first drug identification information stored in the storage unit does not match the second drug identification information read by the reader, the control unit causes the medical pump to be brought into a liquid feeding prohibition mode in which feeding of the drug in the second syringe by the medical pump is prohibited.

* * * * *